(12) United States Patent
Andreaco et al.

(10) Patent No.: US 6,288,399 B1
(45) Date of Patent: Sep. 11, 2001

(54) DEPTH OF INTERACTION DETECTOR BLOCK FOR HIGH RESOLUTION POSITRON EMISSION TOMOGRAPHY

(75) Inventors: Mark S. Andreaco, Knoxville; Charles W. Williams, Powell; Michael E. Casey; Ronald Nutt, both of Knoxville, all of TN (US)

(73) Assignee: CTI Pet Systems, Inc., Knoxville, TN (US)

( * ) Notice: Subject to any disclaimer, the term of this patent is extended or adjusted under 35 U.S.C. 154(b) by 0 days.

(21) Appl. No.: 09/190,661

(22) Filed: Nov. 12, 1998

Related U.S. Application Data
(60) Provisional application No. 60/065,386, filed on Nov. 12, 1997.

(51) Int. Cl.⁷ .................................................. G01T 1/164
(52) U.S. Cl. ...................... 250/368; 250/367; 250/363.03
(58) Field of Search ......................... 250/363.03, 363.01, 250/363.02, 366, 367, 368

(56) References Cited

U.S. PATENT DOCUMENTS

| | | |
|---|---|---|
| 4,843,245 | 7/1989 | Lecomte . |
| 5,122,667 * | 6/1992 | Thompson ...................... 250/363.03 |
| 5,319,204 | 6/1994 | Wong . |
| 5,453,623 | 9/1995 | Wong et al. . |
| 5,753,917 * | 5/1998 | Engdahl ............................... 250/367 |

OTHER PUBLICATIONS

Murakami et al, "A Simple Pulse Shape Discrimination Method for the Phoswich Counter", IEEE Trans. Nuclear Science, vol. 39, No. 5, Oct. 1992.*

K. Herholz, et al.—"Preoperative activation and intraoperative stimulation of language–related areas in glioma patients"*Neurosurgery*, 1997.

L. Fard, et al.—"A PET study of [¹¹C]FLB 457 binding to extrastriatal D2–dopamine receptors in health subjects and antipsychotic drug treated patients" *Psychopharmacology* vol. 133, No. 4, 1997.

(List continued on next page.)

*Primary Examiner*—Georgia Epps
*Assistant Examiner*—Richard Hanig
(74) *Attorney, Agent, or Firm*—Pitts & Brittian, P.C.

(57) ABSTRACT

A depth of interaction detector block for improving the spatial resolution and uniformity in modern high resolution PET systems over an entire FOV. An LSO crystal layer, a GSO crystal layer, and a light guide are stacked on each other and mounted on a 2×2 PMT set, so that the corners of the phoswich are positioned over the PMT centers. The crystal phoswich is cut into a matrix of discrete crystals. The separation of the LSO and the GSO layers by pulse shape discrimination allows discrete DOI information to be obtained. The block design provides an external light guide used to share the scintillation light in four PMTs. The 4 PMT signals $S_i$ are connected to an amplifier box which offers a 4 pole semi-Gaussian shaping for each of the four PMT signals, a sample clock for triggering the ADC cards and a fast sum signal $\Sigma_i S_i$ of the four PMT signals $S_i$ for pulse shape discrimination. A CFD provides a START signal for the time to pulse height converter. The fast sum signal is in addition differentiated and integrated with a fast filter amplifier and connected to a CFD, which provides a STOP signal for the TAC. The outputs of the shaped PMT signals and the TAC are connected to two ADC cards running under computer control.

3 Claims, 7 Drawing Sheets

OTHER PUBLICATIONS

M.E. Casey, et al.—"A multi-crystal two dimensional BGO detector system for positron emission tomography" *IEEE Trans. Nucl Sci.,* vol. 33, pp. 460–463, 1986.

C.L. Melcher, et al.—"Cerium-doped lutetium oxyorthosilicate: A fast, efficient new scintillator" *IEEE Trans. Nucl. Sci.,* vol. 39, No. 4, pp. 502–505, 1992.

W.J. Jagust, et al.—"The cortical topography of temporal lobe hypometabolism in early Alzheimer's disease" *Brain Research,* vol. 629, No. 2, pp 189–198, 1993.

C. Carrier, et al.—"Design of a high resolution positron emission tomograph using solid state scintillation detectors" *IEEE Trans. Nucl. Sci.* vol. 35, No. 1, pp 685–690, 1988.

M.E. Casey, et al.—"Investigation of LSO crystals for high resolution positron emission tomography" *IEEE Trans. Nucl. Sci.,* vol. 44, No. 3, pp. 1109–1113, 1997.

M. Dahlbom, et al.—"Performance of a YSO/LSO Detector Block for use in a PET/SPECT System" IEE Trans. Nucl. Sci. Symposium, vol. 2 p. 1049 (Nov. 1996).

M. Schmand, et al—"Performance results of a new DOI detector block for a High Resolution PET—LSO Reseach Tomograph HRRT", Nov. 12, 1997, IEE Nucl. Sci. Symposium p. 934, vol. 2.

\* cited by examiner

DEPTH OF INTERACTION DETECTOR BLOCK FOR HIGH RESOLUTION POSITRON EMISSION TOMOGRAPHY

This application claims the benefit of U.S. Provisional Application No. 60/065,386, filed Nov. 12, 1997.

TECHNICAL FIELD

This invention relates to the field of positron emission tomography devices. More particularly, the present invention is related to a detector block for measuring depth of interaction activity in high performance positron emission tomography.

BACKGROUND ART

In the field of positron emission tomography, or PET, it is well known that in order to improve the capability for investigating the living human brain, for example, with regard to blood flow, metabolism and receptor characteristics for small structures such as cortical sublayers and nuclei, the spatial resolution has to be improved relative to what is available today, as disclosed by K. Herholz, et al., "Preoperative activation and intraoperative stimulation of language-related areas in glioma patients," Neurosurgery, 1997; and L. Farde, et al., "A PET study of [$^{11}$C]FLB 457 binding to extrastriatal D2-dopamine receptors in health subjects and antipsychotic drug treated patients," Psychopharmacology, vol. 133, no. 4, 1997, spatial resolution of 2 mm or less may be necessary to reach these research goals. Such a resolution approaches the physical limits of the annihilation process itself; the range of positron in tissue and the non-collinearity of the annihilation photons.

The highest spatial resolution positron camera system commercially available for human investigations presently is the ECAT EXACT HR, as discussed by M. E. Casey, et al., "A multi-crystal two dimensional BGO detector system for positron emission tomography," IEEE Trans. Nucl Sci., vol. 33, pp. 460–463, 1986, with a spatial resolution in the reconstructed image planes of less than 4 mm. The ECAT EXACT HR system uses cost effective block technology and is based on BGO scintillators with 7×8 crystals per block with individual crystal sizes of approximately 2.9×5.9×30 mm$^3$. By reducing the geometry of the system, the non-collinearity of the annihilation gamma rays are reduced, resulting in a spatial resolution of around 3 mm for a 40 cm diameter system. However, to maintain this resolution over a 20 cm FOV, the DOI in the 30 mm deep crystals must be obtained, which is a challenge with low light yield scintillators, such as BGO or GSO. Also the time response of the used scintillator has to accommodate an excellent timing resolution to suppress random coincidences with a short coincidence window of ~5 ns. In addition, with the low light from BGO, the 3 mm crystal dimension is probably a practical lower limit which can be resolved with the present BGO based block technology. A cost effective BGO positron camera system based on the block concept with a 2 mm spatial resolution has not been shown to be possible to construct.

Recently a new scintillator has become available, lutetium-oxyorthosilicate (LSO) with a scintillation light yield between four to five times that of BGO and a scintillation decay time of around 40 ns, as disclosed by C. L. Melcher, et al., "Cerium-doped lutetium oxyorthosilicate: A fast, efficient new scintillator," IEEE Trans. Nucl. Sci., vol. 39, no. 4, pp. 502–505, 1992. The high light yield implies that small crystals now can be identified with the block technology with only a small identification degradation due to photon statistics. The short scintillation decay time implies low dead time losses in the detectors. In addition, detectors based on LSO have a good time resolution which offers the possibility of using a short coincidence time window thus reducing the random coincidence contribution. Positron camera systems with a spatial resolution of 2 mm or less are now feasible for investigations of the living human brain as well as for animal studies.

Other related articles include: W. J. Jagust, et al., "The cortical topography of temporal lobe hypometabolism in early Alzheimer's disease", Brain Research, vol. 629, no. 2, pp. 189–198, 1993; C. Carrier, et al., "Design of a high resolution positron emission tomograph using solid state scintillation detectors," IEEE Trans. Nucl. Sci., vol. 35, no. 1, pp. 685–690, 1988; and M. E. Casey, et al., Investigation of LSO crystals for high resolution positron emission tomography," IEEE Trans. Nucl. Sci., vol. 44, no. 3, pp. 1109–1113, 1997. Carrier, et al., disclose a phoswich combination of scintillator detectors for use in a high resolution positron emission tomograph.

An ECAT HRRT, as discussed by Casey, et al., is an octagonal design with 8 detector heads and an axial dimension of 25.2 cm. The distance between two opposing heads is 46.9 cm. Because of the small ring diameter and the large axial and transaxial width, corrections for depth-of-interaction is required to meet the ambitious goal of ~2 mm spatial resolution. The depth-of-interaction information is extracted from differences in scintillation decay time between the two crystal layers. Casey also disclosed the possibilities to use a LSO-LSO combination of the same dimensions using the differences in scintillation decay time.

An object of the present invention is to provide a new block detector for a new brain camera design, the ECAT HRRT, with a phoswich combination of LSO and GSO crystals with an individual crystal sizes, for example, of around 2.1×2.1×7.5 mm$^3$ in each crystal layer.

DISCLOSURE OF THE INVENTION

Other objects and advantages will be accomplished by the present invention which is provided for improving the spatial resolution and uniformity in modem high resolution brain Positron Emission Tomography (PET) systems over the entire field of view (FOV). An LSO crystal layer, a GSO crystal layer, and a light guide are stacked on each other and mounted on a 2×2 photomultiplier tube (PMT) set, so that the corners of the phoswich are positioned over the PMT centers. The crystal phoswich is cut into a matrix of discrete crystals. The separation of pulses from the LSO and the GSO layers by pulse shape discrimination allows discrete DOI information to be obtained. The block design provides an external light guide used to share the scintillation light in four PMTs.

The 4 PMT signals $S_i$ are connected to an amplifier box which offers a 4 pole semi-Gaussian shaping for each of the four PMT signals, a sample clock for triggering the ADC cards and a fast sum signal $\Sigma_i S_i$ of the four PMT signals $S_i$ for pulse shape discrimination. A constant fraction discriminator (CFD) provides a START signal for the time to pulse height converter. The fist sun signal is in addition differentiated and integrated with a fast filter amplifier and connected to a CFD, which provides a STOP signal for the TAC. The outputs of the shaped PMT signals and the TAC are connected to two ADC cards running under computer control.

For the flood source measurements, both cards are triggered with the sample clock signal of the amplifier box, initialized by the sum signal of the four PMTs. For the line spread function measurements, the CFD signal initialized by the sum signal and the CFD signal initialized by the reference detector are connected to a coincidence board. The reference detector is a single GSO crystal mounted on a single PMT. The PMT signal is amplified and connected to a CFD. The CFD signal in coincidence with the block CFD signal gives the trigger for the ADC cards. The data are acquired on the computer in list mode or directly as histogram data and are then transferred for analysis. A flood source is placed a selected distance from the crystal face to uniformly irradiate the block. The ADC card trigger line is connected to the sample clock. Software is provided for analyzing the data for identification of each single LSO and GSO crystal and for calculation of the events, energy centroid and energy resolution per crystal. The data are processed in two separate runs. The first run is to determine the thresholds in the zero cross time spectrum of the pulse shape discrimination data. The acquired time entries in the list mode data are sorted into a histogram. A double Gaussian is fit to the data to define the time boundaries, identifying the layer of the event interaction. A low and a high threshold for all accepted cross over times is set to 5% of the fit peak maximum of the LSO (low) and the GSO (high) in the time distribution spectrum. The intermediate threshold is set to the minimum between the two peaks.

In the second run the list mode data are sorted for LSO and GSO by the list mode time entries in the lower and the upper time window. Events outside the time windows are rejected. The energy spectrum for each layer is histogrammed and energy thresholds are computed based on Gaussian fit to the photo peak. Interactive changes of the energy thresholds for background suppression and time thresholds for cross talk minimization between the layers are possible and reprocessing of the list mode data is performed automatically. The two two-dimensional positioning histograms for LSO and GSO are calculated from the four PMT signals $S_i$, simultaneously.

In order to obtain the relevant performance data with high statistics, the definition file is brought to the measurement computer and a selected number of events are acquired. During this acquisition, energy and events are histogrammed for every single crystal based on the time, the layer, and energy thresholds and the crystal look-up table for crystal identification. Also, the time spectra for every LSO/GSO pair is stored. The histogram data are transferred to the computer for display and analysis. The energy centroid, which is the sum over all four PMT signals $\Sigma_i S_i$, and energy resolution of each single crystal is achieved by fitting a Gaussian function after background subtraction to the photo peak in the histogram data.

To determine the intrinsic resolution of the detector block, an opposing reference detector is placed a selected distance in front of the block. The detector block is mounted in a fixed position. The reference detector is positioned in different angles with respect to the block where the distance between the crystal front faces of the block and the reference is given by a circle of selected radius. A glass capillary filled with $^{18}F$ water solution is used as a line source. The line source is placed in the middle of the center line between the block and the reference detector and attached to a stepper motor. The measurement is performed for 0°, 45°, and 90° angles. To calculate the line spread function (LSF), the list mode data are transferred to the computer and the events per crystal are computed for each of the single crystals. The registered events are plotted over the source step positions for every single detector crystal in the block.

BRIEF DESCRIPTION OF THE DRAWINGS

The above mentioned features of the invention will become more clearly understood from the following detailed description of the invention read together with the drawings in which.

BEST MODE FOR CARRYING OUT THE INVENTION

The present invention is provided for improving the spatial resolution and uniformity in modern high resolution brain Positron Emission Tomography (PET) systems over the entire field of view (FOV). Specifically, the present invention is provided for archiving the depth of interaction (DOI) information and for correcting for spatial resolution degradation. Described herein is the incorporation of the present invention into a high resolution lutetium-oxyorthosilicate/germanium-oxyorthosilicate (LSO/GSO) phoswich block detector with DOI capability.

An LSO crystal layer, a GSO crystal layer, and a light guide are stacked on each other and mounted on a 2×2 photomultiplier tube (PMT) set, so that the corners of the phoswich are positioned over the PMT centers. One PMT used with success is the Hamamatsu R-1450. In one embodiment of the present invention, the crystal layers and the light guide measure approximately 19×19×7.5 mm. However, it will be understood that the dimensioning may be varied depending upon the desired results and applications. Specifically, the width and breadth of each layer is dimensioned to equal the center-to-center dimension of the adjacent PMT's. In the illustrated embodiment, the crystal phoswich is cut into an 8×8 matrix of discrete crystals, to yield 64 crystals in each of the LSO and GSO layers, for a total of 128 crystals. The separation of the LSO and the GSO layers by pulse shape discrimination allows discrete DOI information to be obtained. The high light output and the light guide design results in an accurate identification of the 128 single crystals per block. Flood source measurements from the illustrated embodiment document a very good homogeneity of events, energy centroid stability and energy resolution (14–20% FWHM per single crystal In the illustrated embodiment, an intrinsic resolution ~1.3 mm and the DOI feasibility is extracted by coincidence measurements with a single 2×2×7.5 mm³ GSO crystal.

Figure 1:
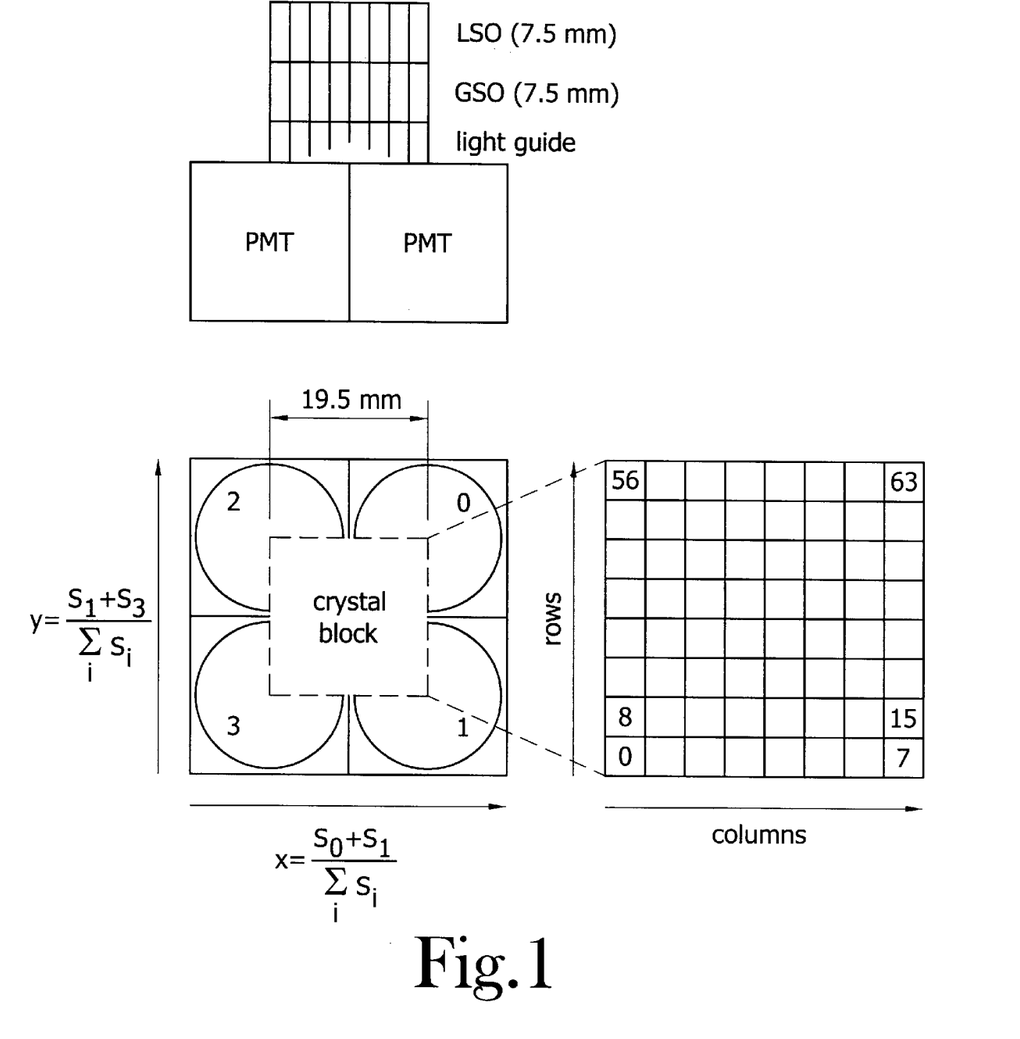
FIG. 1A is a schematic illustration of a top plan view of a detector block setup in accordance with several features of the present invention.
FIG. 1B is a schematic illustration of a side elevation view of the detector block setup of FIG. 1A showing the light guide and the LSO and GSO scintillator layers.

The block design of FIG. 1 is similar to previously published designs such as those disclosed in M. E. Casey, et al., "A multi-crystal two dimensional BGO detector system for positron emission tomography," *IEEE Trans. Nucl. Sci.*, vol. 33, pp. 460–463, 1986; and Wai-Hoi Wong, "A positron camera design with cross-coupled scintillators and quadrant sharing photomultipliers," *IEEE Trans. Nucl. Sci.*, vol. 40, no. 4, pp. 962–966, 1993. However, in contrast to those previous disclosures, the present invention provides an external light guide used to share the scintillation light in four PMTs. In the illustrated embodiment, the PMTs define a diameter of ~19 mm and are cast in RTV with a 19.5 mm center-center spacing, which matches the crystal dimension with a reflector coating. The illustrated block detector is a segment of an ECAT HRRT detector panel.

Figure 2:
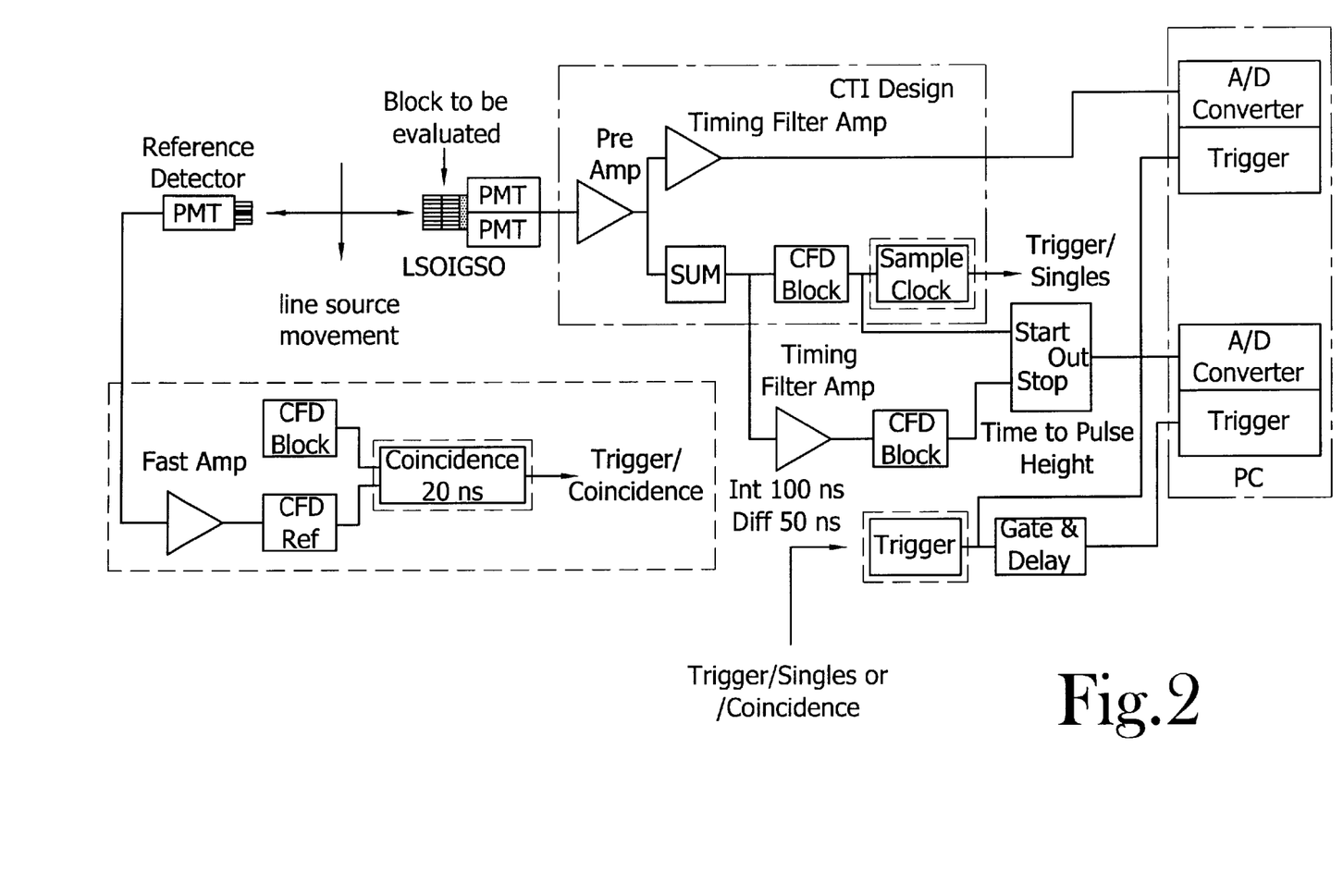
FIG. 2 is a schematic illustration of the electronic circuitry of the present invention.

FIG. 2 is a schematic illustration of the electric circuitry used in the present invention. The 4 PMT signals $S_i$ are connected to an amplifier box which offers a 4 pole semi-Gaussian shaping with a shaping time of 91 ns for each of the four PMT signals, a sample clock for triggering the ADC cards and a fist sum signal $\Sigma_i S_i$ of the four PMT signals $S_i$ for pulse shape discrimination. A constant fraction discriminator (CFD) provides a START signal for the time to pulse height converter. The fist sum signal is in addition differentiated (for example, 50 ns) and integrated (for example, 100 ns) with a fast filter amplifier and connected to a CFD, which provides a STOP signal for the TAC. The outputs of the shaped PMT signals and the TAC are connected to two ADC cards such as those manufactured by National Instruments, Part No. A2000, running under computer control.

For the flood source measurements, both cards are triggered with the sample clock signal of the amplifier box, initialize by the sum signal of the four PMTs. For the line spread function measurements, the CFD signal initialized by the sum signal and the CFD signal initialized by the reference detector are connected to a coincidence board with a 20 ns time window, as illustrated in FIG. 2 at "Trigger/Coincidences". The reference detector in the illustrated embodiment is a single 2×2×7.5 mm³ GSO crystal mounted on a single PMT such as the previously disclosed Hamamatsu R-1450. The PMT signal is amplified and connected to a CFD. The CFD signal in coincidence with the block CFD signal gives the trigger for the ADC cards. The data are acquired on the computer in list mode or directly as histogram data and are then transferred for analysis.

Figure 3:
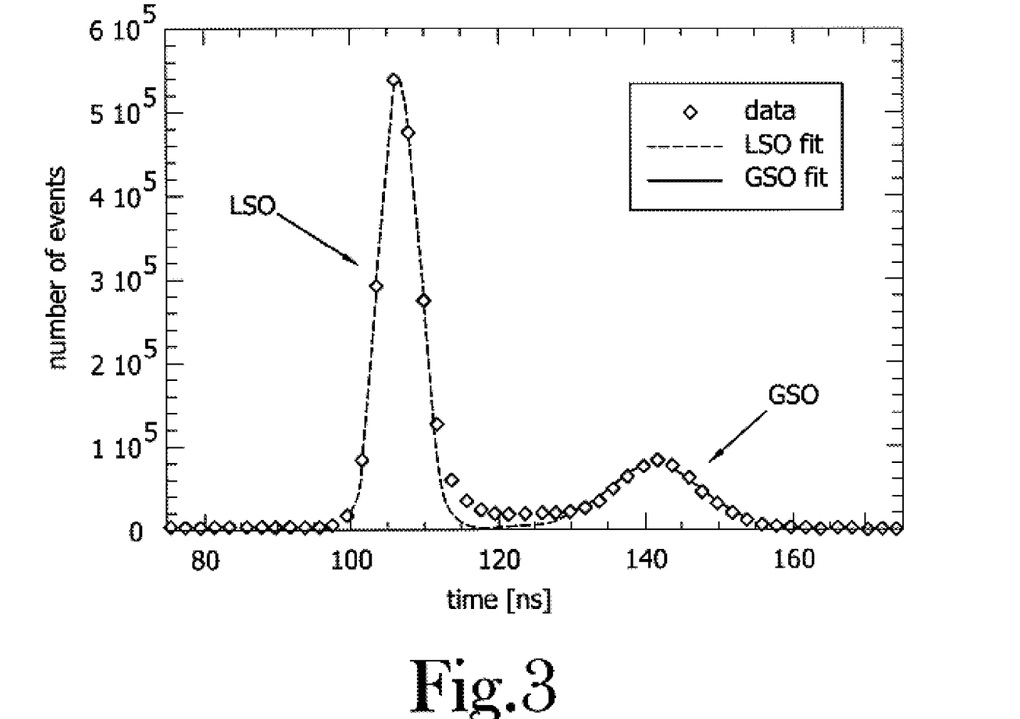
FIG. 3 is an exemplary histogram illustrating a time cross over spectrum for achieving depth of interaction.

For a flood source measurement, a ⁶⁸Ge flood source is placed 10 cm from the crystal face to uniformly irradiate the block. The ADC card trigger line is connected to the sample clock, as illustrated in FIG. 2 at "Trigger/Single". In the illustrated embodiment, two million events are acquired in list mode and the data stream is transferred to the workstation. Software is provided for analyzing the data for identification of the 128 single LSO and GSO crystals and for calculation of the events, energy centroid and energy resolution per crystal. The data are processed in two separate runs. The first run is to determine the thresholds in the zero cross time spectrum of the pulse shape discrimination data. The acquired time entries in the list mode data are sorted into a histogram, as illustrated in FIG. 3. A double Gaussian is fit to the data to define the time boundaries, identifying the layer of the event interaction. A low and a high threshold for all accepted cross over times is set to 5% of the fit peak maximum of the LSO (low) and the GSO (high) in the time distribution spectrum. The intermediate threshold is set to the minimum between the two peaks.

In the second run the list mode data are sorted for LSO and GSO by the list mode time entries in the lower and the upper time window. Events outside the time windows are rejected The energy spectrum for each layer is histogrammed and energy thresholds are computed based on Gaussian fit to the photo peak. Interactive changes of the energy thresholds for background suppression and time thresholds for cross talk minimization between the layers are possible and reprocessing of the list mode data is performed automatically. The two two-dimensional positioning histograms for LSO and GSO are calculated from the four PMT signals $S_i$ simultaneously. The calculation of the X and Y histogram position for every single event is done by the Anger logic principle:

$$X = \frac{S_0 + S_1}{\sum_i S_i};$$

$$Y = \frac{S_1 + S_3}{\sum_i S_i}.$$

Figure 4:
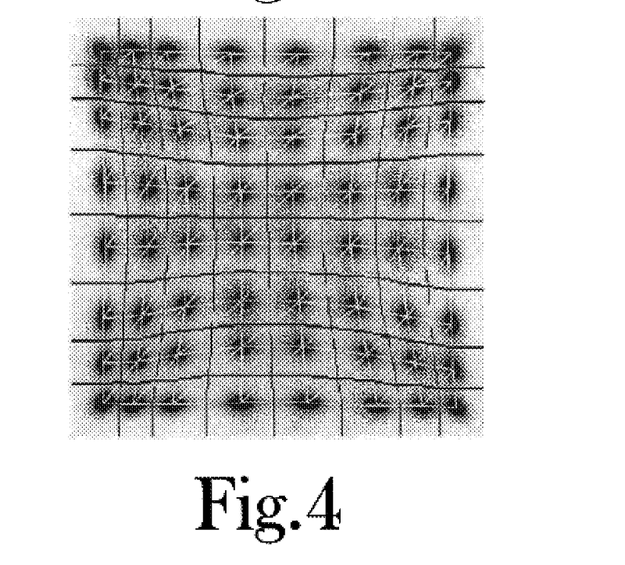
FIG. 4 is an exemplary two-dimensional histogram for the LSO layer showing calculated crystal boundaries and peak-to-peak paths.

A typical 2D positioning histogram for the LSO layer is shown in FIG. 4. The single crystals are represented by the 64 peaks in the 2D histogram To identify the crystals, crystal boundaries, seen as black lines in FIG. 4, are calculated based on the minima between the crystal peak maximum and the eight surrounding maxima. A binary look-up table is created and stored in a definition file. The definition file contains also the optimized energy and time thresholds to be able to do an on-line histogramming for high statistics.

In order to obtain the relevant performance data with high statistics, the definition file is brought to the measurement PC and 300 million events are acquired. During this acquisition, energy and events are histogrammed for every single crystal based on the time, the layer, and energy thresholds and the crystal look-up table for crystal identification. Also, the time spectra for every LSO/GSO pair is stored. The histogram data are transferred to the computer for display and analysis. The energy centroid, which is the sum over all four PMT signals $\Sigma_i S_i$, and energy resolution of the 128 single crystals is achieved by fitting a Gaussian function after background subtraction to the photo peak in the histogram data.

Figure 5:
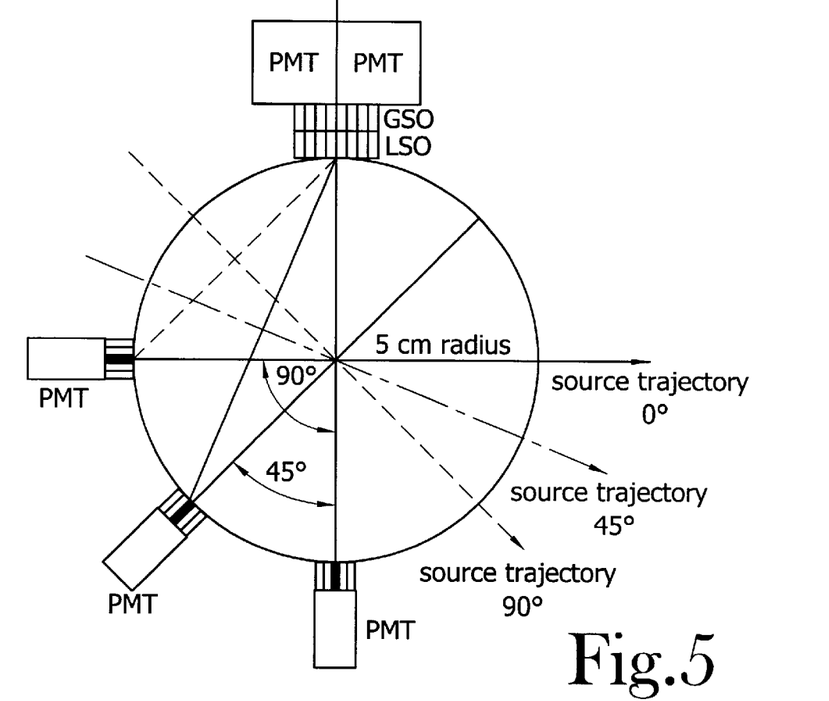
FIG. 5 illustrates a line spread function setup of the present invention.
Figure 9:
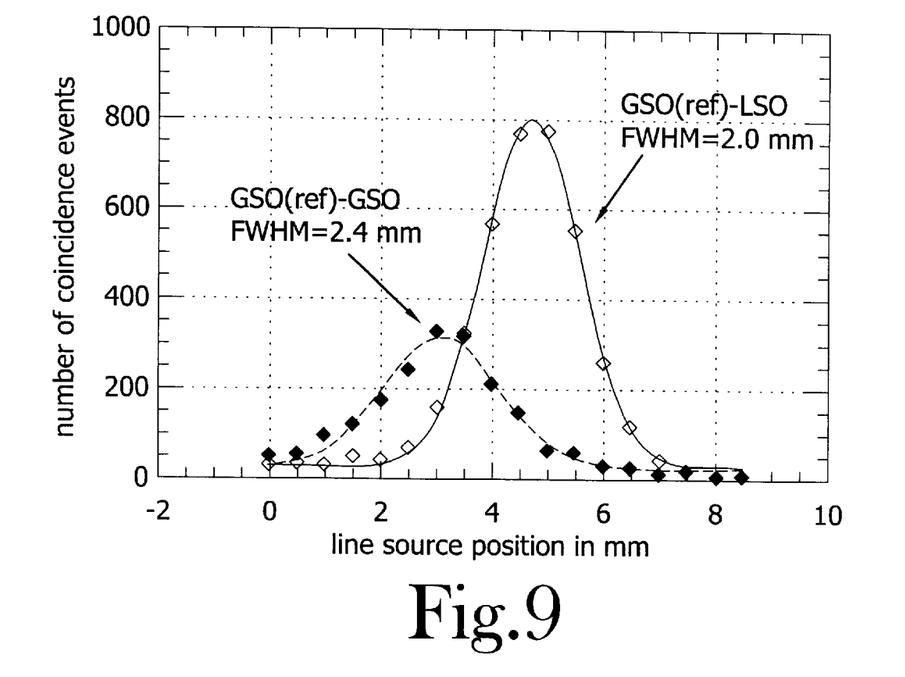
FIG. 9 is a graphical representation of the separation between the line spread function data in an LSO peak and a GSO peak.

To determine the intrinsic resolution of the detector block, an opposing reference detector is placed 10 cm, as illustrated in FIG. 5, in front of the block. The reference detector is a single 2×2×7.5 mm³ GSO crystal surrounded by 24 light-isolated GSO crystals with the same dimension to provide a proper scatter environment, mounted on a PMT. The detector block is mounted in a fixed position. The reference detector can be positioned in different angles with respect to the block where the distance between the crystal front faces of the block and the reference is given by a 5 cm radius circle. A glass capillary with an inner diameter of ~0.25 mm filled with ¹⁸F water solution is used as a line source. The line source is placed in the middle of the center line between the block and the reference detector and attached to a stepper motor. The motor provides a source movement perpendicular to the connecting line with a step size of 0.5 mm. For the measurement, the line source is moved in 20 steps starting 5 mm off center line. 20,000 coincidence events are acquired for each step. The measurement is performed for 0°, 45°, and 90° angles. To calculate the line spread function (LSF), the list mode data are transferred to the computer and the events per crystal are computed for each of the 128 single crystals, using the program described above. The registered events are plotted over the source step positions for every single detector crystal in the block. FIG. 9 shows the two LSF of crystal pair 18 (illustrated in FIG. 1) for the LSO layer ($GSO_{ref}$-LSO) and the GSO layer.

In the positioning histogram illustrated in FIG. 4, all of the 64 LSO and all of the 64 GSO crystals in the block are identifiable. In this figure, a very good valley to peak ratio is observed. Connection lines between the peaks, or peak-to-peak paths, are 1-dimensional cuts through the 2D positioning histogram and are illustrated as white lines in FIG. 4. To evaluate the crystal identification probability, the valley to peak ratio $VPR_i$ for most of the connection lines (161) between adjacent peaks are calculated by building the ratio of the minimum ($Min_i$.) and the average peak maximum ($Max_i$) of the two maxima ($Max_{ij}$):

$$VPR_i = \frac{Min_i}{\frac{Max_{i,1} + Max_{i,2}}{2}}.$$

The diagonal peak-to-peak paths in the illustration of FIG. 4 are only calculated for one direction-from the lower left towards the upper right corner. Calculating the paths in one direction and finding the minimum $Min_i$ is sufficient for calculating the crystal look-up table. The paths perpendicular in a perfect grid with homogenous spacing do not add any additional information.

Figure 8:
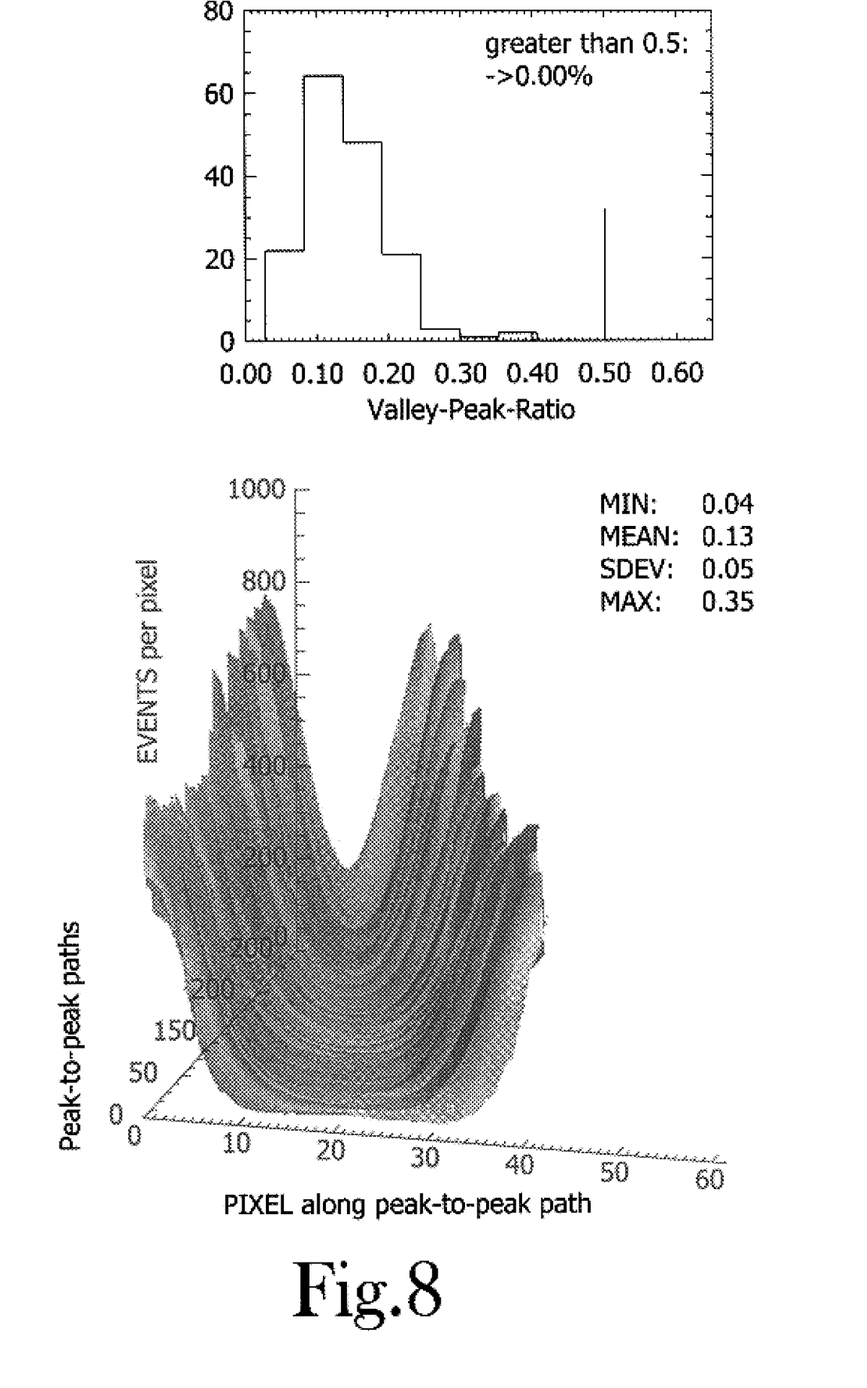
FIG. 8 is a graphical representation of the valley-to-peak ratio for an LSO/LSO HRRT block.

A surface plot of the peak-to-peak paths from a LSO/LSO block, sorted by the number of pixels illustrate the excellent separation between adjacent peaks. The histogrammed $VPR_i$, as illustrated in FIG. 8, for one particular LSO/LSO block which has been tested, has a mean value of $VPR_i=$ 0.11. Most of $VPR_i$ for the LSO/GSO block are better than 0.3 with a mean value $VPR_{mean} < 0.24$ for both layers. The improvement is based on improving the light guide design for the block. The $VPR^i$ are less than 0.2, which results in a crystal identification probability better than 94%. The 94% probability is calculated from two Gaussian functions with a valley to peak ratio of VPR=0.2.

Figure 6:
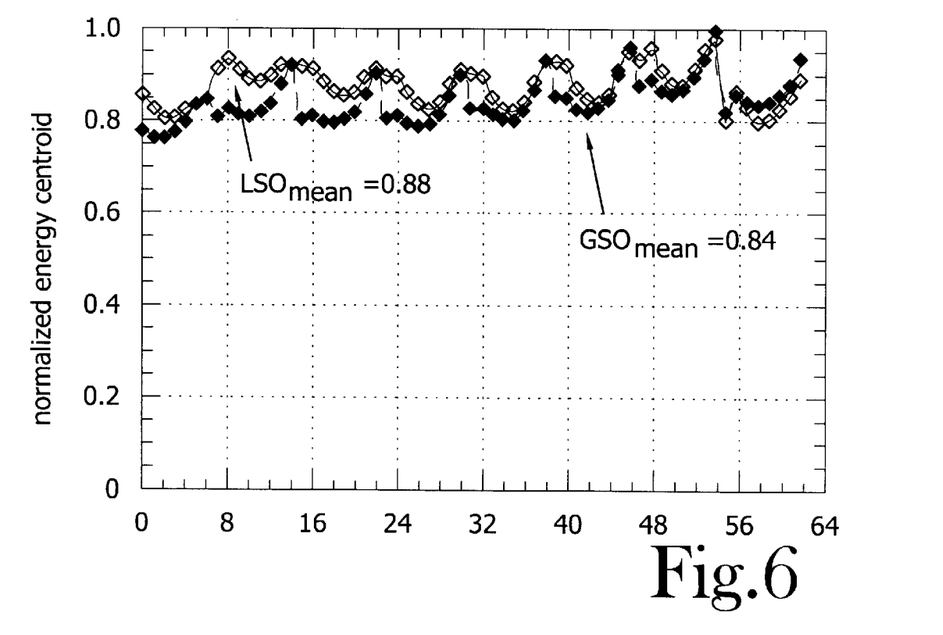
FIG. 6 is a graphical representation of the normalized energy centroid for each LSO and GSO crystal.
Figure 7:
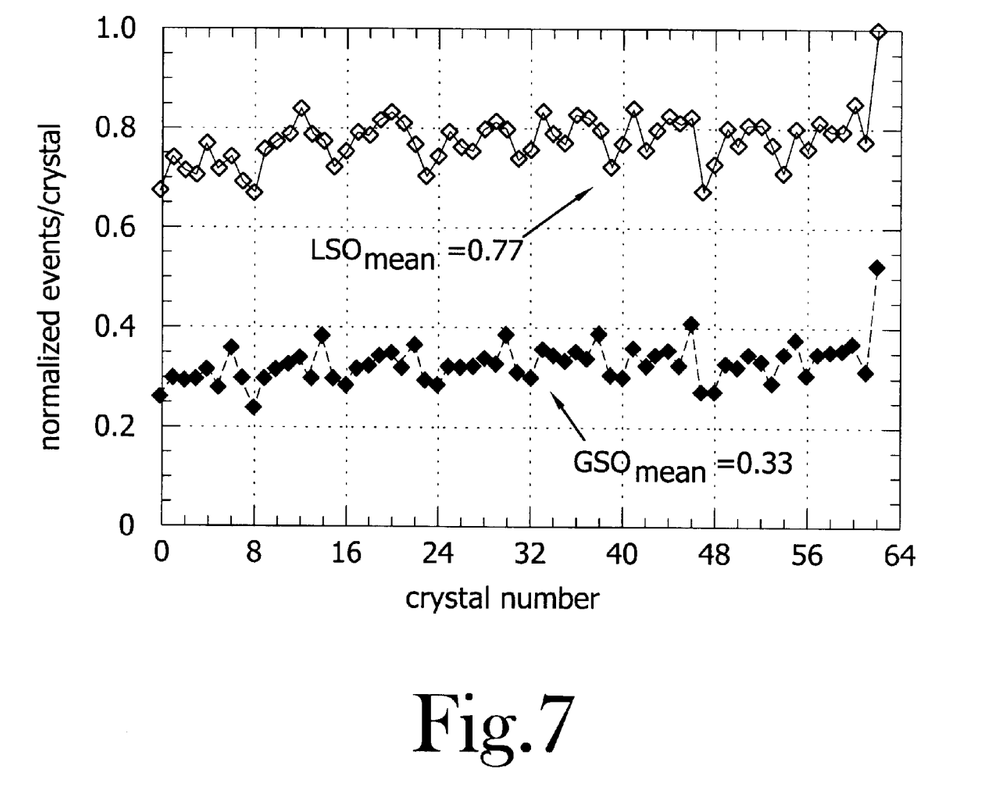
FIG. 7 is a graphical representation of the count rate response for each LSO and GSO crystal.

The calculated events, as schematically quantified in FIG. 7, and energy centroid, as depicted in FIG. 6, per crystal are normalized of the maximum value of the 128 crystals and plotted for both layer over all 64 crystals. The energy resolution varies between 14–18% for the LSO crystals and between 16–20% for the GSO crystals. The uniformity of the positions of the individual photopeak centroids is shown in FIG. 6, wherein the standard deviation is less than 6% for both layers, thus making it feasible to use only one lower and upper energy threshold for each crystal layer. The count rate response in the illustrated example was also found to be uniform as demonstrated by FIG. 7, wherein the observed variation in count rate for the LSO layer is less than 7% and less than 13% for the GSO layer. The average count rate of LSO over the GSO count rate gives a ratio of 2.4±0.3. The value matches well within the error limits with the theoretical ratio of 2.23.

A Gaussian function is fitted to all of the 64+64 LSO and GSO LSF plots for each of the three measured angle positions from which the intrinsic resolution as the FWHM were extracted. An example of the 45° study is shown in FIG. 9, demonstrating the separation between the line spread function data in a LSO peak and in a GSO peak. The distance between the peak maxima in position space is consistent with the angular setup, assuming the peak maxima is identical with the center of gravity for the single crystals. For 15 mm detectors, the resolution is estimated to be degraded to ~3.5 FWHM, by convolving the two Gaussian fits of the LSO and the GSO layer.

TABLE 1

Intrinsic resolution in [mm] for the study (FIG. 5) and for the corrected HRRT geometry

|  | LSO | | GSO | |
|---|---|---|---|---|
|  | study | corrected | study | corrected |
| 0° | 1.35 | 1.60 | 1.49 | 1.72 |
| 45° | 2.07 | 2.21 | 2.47 | 2.59 |
| 90° | 3.18 | 3.45 | 3.45 | 3.51 |

Figure 10:
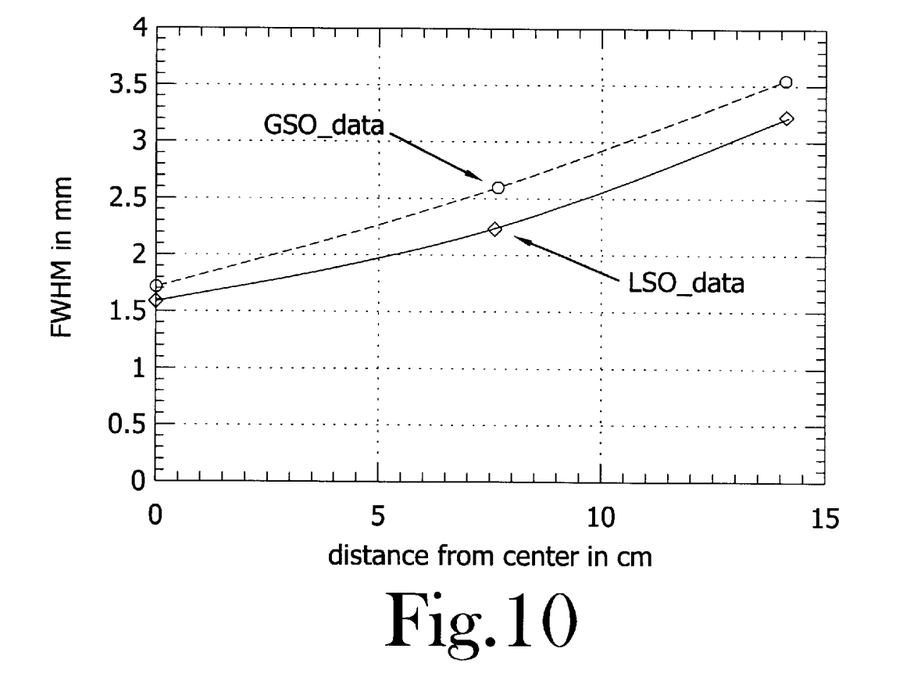
FIG. 10 is a graphical representation of corrected measured data representing the intrinsic resolution with respect to distance from the center of the field of view.

The intrinsic spatial resolution data are summarized in Table 1. To predict the intrinsic resolution for the ECAT HRRT, the measured data, listed in the "study" column, are corrected for the non-collinearity of the annihilation photon pair in a ~50 cm ring diameter, as listed in the "corrected". A polygon fit to the corrected measured data is illustrated in FIG. 10 and represents the intrinsic resolution for all effective detector block combinations in the ECAT HRRT in distance out of the center of the FOV, showing the feasibility to obtain a reconstructed resolution of less than 2.5 mm within the dimensions of a 10 cm FOV. The data points (○,◇) are the results for the 0°, 45° and 90° study extrapolated for a 25 cm ring radius, in lieu of the 5 m example depicted in FIG. 5, and converted in distance out of center of the FOV, 0 cm, 7.7 cm and 14.2 cm, respectively. In addition, the results indicate that the block identification capability does not add extra uncertainties into to the spatial resolution.

Flood source measurements show the feasibility to clearly identify the signals from the two different crystal layer LSO and GSO and the identification of all single crystals per block. The homogeneity of events, energy centroid and energy resolution of 14–20% FWHM per crystal is significantly better than well characterized BGO blocks. Coincidence measurements with a single GSO (2×2×7.5 mm$^3$) crystal demonstrate the DOI capability of the ECAT HRRT detector block and an intrinsic resolution of ~1.3 for the GSO(ref)-LSO layer combination In the present invention, a LSO/GSO phoswich detector combination bas been implemented to improve sensitivity and timing of a high resolution PET system The present invention makes it feasible to achieve the discrete DOI information by pulse shape discrimination with 7 ns difference in the light decay time of the two layers. The results for an LSO front-front layer combination are improved because of better stopping power of the LSO layer as a reference detector instead of GSO, but also the intrinsic resolution for a back-back layer combination are degraded because of scattered events in the front layer, which was not existing in the single GSO layer of the reference detector in the described measurement above. As a result of the present invention, it is feasible to build the ECAT HRRT as a pure LSO scanner with DOI capability and a spatial resolution of ~2 mm. over a 10 cm FOV.

While an illustrated embodiment has been shown and described, it will be understood that it is not intended to limit the disclosure, but rather it is intended to cover all modifications and alternate methods falling within the spirit and the scope of the invention as defined in the appended claims. Further, although particular values have been provided for the illustrated embodiments and examples, it will be understood that the individual values do not constitute the present invention, and may be varied depending upon the particular application of the present invention.

Having thus described the aforementioned invention, we claim:

1. A depth of interaction detector block for high resolution positron emission tomography comprising:

a light guide positioned above a 2×2 matrix of photomultiplier tubes, each of said photomultiplier tubes defining a geometric center, said light guide defining an area defined by four corners, one each of said four corners being coincident with said geometric center of one of said photomultiplier tubes, said light guide being provided for sharing scintillation light emitted to said photomultiplier tubes, signals from said photomultiplier tubes being connected to an amplifier, said amplifier including four-pole semi-Gaussian shaping for said signals, a sample clock for triggering at least one ADC card, a fast sum signal of said signals for pulse shape discrimination;

a first layer of scintillator crystals defining an area substantially equal to said light guide, said first layer of scintillator crystals being stacked on said light guide;

a second layer of scintillator crystals defining an area substantially equal to said light guide, said second layer of scintillator crystals being stacked on said first layer of scintillator crystals, the pulses from said first and second layers of scintillator crystals being separated by pulse shape discrimination.

2. The depth of interaction detector block for high resolution positron emission tomography of claim 1 wherein said first layer of scintillator crystals is fabricated from GSO.

3. The depth of interaction detector block for high resolution positron emission tomography of claim 1 wherein said second layer of scintillator crystals is fabricated from LSO.

* * * * *